(12) United States Patent
Lee et al.

(10) Patent No.: US 8,911,775 B2
(45) Date of Patent: Dec. 16, 2014

(54) PH-SENSITIVE BLOCK COPOLYMER FORMING POLYIONIC COMPLEX MICELLES AND DRUG OR PROTEIN CARRIER USING THE SAME

(75) Inventors: Doo Sung Lee, Gwacheon Si (KR); Bong Sup Kim, Suwon-si (KR); Jung Hee Lee, Seoul (KR); Guanghui Gao, Suwon-si (KR)

(73) Assignee: Sungkyunkwan University Foundation for Corporate, Suwon-Si (KR)

( * ) Notice: Subject to any disclaimer, the term of this patent is extended or adjusted under 35 U.S.C. 154(b) by 675 days.

(21) Appl. No.: 12/842,388

(22) Filed: Jul. 23, 2010

(65) Prior Publication Data

US 2011/0150978 A1 Jun. 23, 2011

(30) Foreign Application Priority Data

Dec. 22, 2009 (KR) .................. 10-2009-0129102
May 27, 2010 (KR) .................. 10-2010-0049623

(51) Int. Cl.
| | | |
|---|---|---|
| *A61K 38/38* | (2006.01) | |
| *C08G 73/06* | (2006.01) | |
| *A61K 9/127* | (2006.01) | |
| *A61P 35/00* | (2006.01) | |
| *A61P 9/10* | (2006.01) | |
| *A61P 29/00* | (2006.01) | |
| *A61P 19/02* | (2006.01) | |
| *C08L 71/02* | (2006.01) | |
| *C08F 299/02* | (2006.01) | |
| *B82Y 5/00* | (2011.01) | |
| *C08F 290/06* | (2006.01) | |
| *A61K 9/107* | (2006.01) | |

(52) U.S. Cl.
CPC ......... *C08F 290/062* (2013.01); *C08L 2201/06* (2013.01); *C08L 71/02* (2013.01); *C08L 2203/02* (2013.01); *C08G 2261/126* (2013.01); *C08F 299/024* (2013.01); *B82Y 5/00* (2013.01); *C08L 2205/05* (2013.01); *A61K 9/1075* (2013.01)
USPC .............. 424/450; 528/327; 514/152; 514/19

(58) Field of Classification Search
USPC ................. 424/450; 528/327; 514/152, 19
See application file for complete search history.

(56) References Cited

U.S. PATENT DOCUMENTS

| | | | |
|---|---|---|---|
| 6,103,865 A | 8/2000 | Bae et al. | |
| 6,616,946 B1 * | 9/2003 | Meier et al. ................... | 424/489 |
| 6,852,334 B1 * | 2/2005 | Cullis et al. ................... | 424/450 |
| 7,169,411 B1 * | 1/2007 | Kabanov et al. .............. | 424/486 |
| 7,371,781 B2 * | 5/2008 | Bae et al. ................... | 514/772.1 |
| 7,427,394 B2 | 9/2008 | Anderson et al. | |
| 7,951,846 B2 * | 5/2011 | Bae et al. ................... | 514/772.1 |
| 2005/0118425 A1 * | 6/2005 | Childs et al. ................ | 428/402.2 |
| 2005/0129769 A1 * | 6/2005 | Barry et al. ................... | 424/486 |
| 2007/0218120 A1 * | 9/2007 | Lee et al. ...................... | 424/450 |
| 2008/0213379 A1 * | 9/2008 | Bae et al. ...................... | 424/490 |
| 2009/0274753 A1 * | 11/2009 | Bae et al. ...................... | 424/450 |
| 2010/0159019 A1 * | 6/2010 | Yang et al. ..................... | 424/497 |
| 2010/0233264 A1 * | 9/2010 | Lee et al. ...................... | 424/486 |
| 2011/0052679 A1 * | 3/2011 | Hassan et al. ................. | 424/451 |

FOREIGN PATENT DOCUMENTS

| | | | |
|---|---|---|---|
| KR | 10-2002-0096585 A | | 12/2002 |
| WO | WO2008004978 A2 | * | 1/2008 |
| WO | WO-2009/031861 | * | 3/2009 |
| WO | WO 2009031861 A2 | * | 3/2009 |
| WO | WO-2009-084801 | * | 7/2009 |

* cited by examiner

*Primary Examiner* — Frederick Krass
*Assistant Examiner* — Celeste A Roney
(74) *Attorney, Agent, or Firm* — Sughrue Mion, PLLC

(57) ABSTRACT

Disclosed is a pH-sensitive block copolymer that forms polyionic complex micelles. The block copolymer is prepared by copolymerization of (a) a polyethylene glycol compound, (b) a poly(amino acid) compound, and (c) a heterocyclic alkyl amine compound having the ability to induce the formation of ionic complexes. Further disclosed is a drug or protein carrier using the block copolymer.

12 Claims, 10 Drawing Sheets

PH-SENSITIVE BLOCK COPOLYMER FORMING POLYIONIC COMPLEX MICELLES AND DRUG OR PROTEIN CARRIER USING THE SAME

BACKGROUND OF THE INVENTION

1. Field of the Invention

The present invention relates to a pH-sensitive block copolymer that forms polyionic complex (PIC) micelles and a drug or protein carrier using the block copolymer. More specifically, the present invention relates to a pH-sensitive block copolymer that forms nanometer-sized polyionic complex micelles capable of stably containing a drug or protein when administered to a human body through a blood vessel and releasing the drug or protein in response to pH variations at a disease site, and a polymeric micelle-type drug or protein carrier comprising the pH-sensitive block copolymer.

2. Description of the Related Art

Generally, micelles refer to as thermodynamically stable and uniform spherical structures composed of amphiphilic materials (e.g., materials possessing both hydrophilic and hydrophobic groups) of low molecular weight. When a solution of a water insoluble (i.e. hydrophobic) drug is introduced into a compound having a micelle structure, the micelles contain the drug and respond to temperature or pH variations in the body, thus enabling target-specific delivery of the drug. Therefore, the applicability of such micelle type compounds to carriers for drug delivery is considered very high. A key determinant for the applicability of the micelle type compounds is how to stably contain a drug in blood vessels of a human body after administration of a drug through the blood vessel until arrival at a particular disease site, such as a cancer site, to release the drug.

Korean Patent No. 0773078 describes the preparation of micelles using polyethylene glycol and a biodegradable polymer. These constituent materials are advantageously biocompatible due to their biodegradability, but they are not sensitive to changes of particular factors (for example, pH) in the body, making it difficult to deliver a drug to a desired site.

U.S. Pat. No. 6,103,865 discloses a polymer using sulfonamide as a pH-sensitive material. The sulfonamide becomes insoluble at pH≤7.4 but it is ionized and shows acidity at pH>7.4. Since the pH-dependent characteristics of the polymer are opposite to the pH characteristics of cancer cells as targets, the use of a basic compound in the polymer is needed to target the cancer cells. It is known that the pH environment of the body is typically maintained at 7.2-7.4 but the ambient environment of abnormal cells such as cancer cells is weakly acidic (pH 6.0-7.2). In recent years, studies have been done on the specific delivery of drugs to cancer cells at pH<7.2. However, the description that the polymer disclosed in U.S. Pat. No. 6,103,865 can contain a drug and efficiently deliver the drug to a disease site in response to pH variations cannot be found in the specification of the patent because of the poor ability of the polymer to form complexes with the drug.

U.S. Pat. No. 7,427,394 B2 discusses the preparation and application of a biodegradable poly(β-amino ester) compound that is designed to have ester groups associated with biodegradability and tertiary amine groups ionizable at particular pH values in the backbone thereof. The poly(β-amino ester) compound has the advantage that the water solubility varies depending on pH. However, there is no description regarding efficient utilization of the poly(β-amino ester) compound as a drug carrier based on the ionization characteristics.

Under these circumstances, there is a need to develop a copolymer capable of stably containing a drug or protein upon administration to a human body through a route of administration such as a blood vessel and efficiently delivering the drug or protein to a disease site, and a drug or protein carrier using the copolymer.

SUMMARY OF THE INVENTION

The present invention has been made in view of the above problems, and an object of the present invention is to provide a copolymer that can stably contain a drug or protein upon administration to a human body through a route of administration such as a blood vessel and can efficiently deliver the drug or protein to a disease site.

Another object of the present invention is to provide a drug or protein carrier that can stably contain a drug or protein upon administration to a human body through a route of administration such as a blood vessel and can efficiently deliver the drug or protein to a disease site in response to variations in the disease site.

According to an aspect of the present invention, there is provided a pH-sensitive block copolymer forming polyionic complex micelles, which is prepared by copolymerization of: (a) a polyethylene glycol compound; (b) a poly(amino acid) compound; and (c) a heterocyclic alkyl amine compound having the ability to induce the formation of ionic complexes.

In an embodiment, the polyethylene glycol compound has an acrylate or methacrylate group as a monofunctional group at one end thereof.

In an embodiment, the polyethylene glycol compound has a number average molecular weight ($M_n$) of 500 to 5,000 g/mol.

In an embodiment, the poly(amino acid) compound is a poly(β-amino ester) (PAE), a poly(β-amido amine) (PAA) or a copolymer thereof (PAEA).

In an embodiment, the poly(amino acid) compound is prepared by polymerization of a bisacrylate or bisacrylamide compound with a primary or secondary amine compound.

In an embodiment, the bisacrylate compound is selected from the group consisting of ethylene glycol diacrylate, 1,4-butanediol diacrylate, 1,3-butanediol diacrylate, 1,6-hexanediol diacrylate, 1,5-pentanediol diacrylate, 2,5-pentanediol diacrylate, 1,6-hexanediol ethoxylate diacrylate, 1,6-hexanediol propoxylate diacrylate, 3-hydroxy-2,2-dimethylpropyl-3-hydroxy-2,2-dimethylpropionate diacrylate, 1,7-heptanediol diacrylate, 1,8-octanediol diacrylate, 1,9-nonanediol diacrylate, 1,10-decanediol diacrylate, and mixtures thereof and the bisacrylamide compound is N,N'-methylene bisacrylamide (MDA) or N,N'-ethylene bisacrylamide.

In an embodiment, the primary amine compound is selected from the group consisting of 1-methylamine, 1-ethylamine, 1-propylamine, 1-butylamine, 1-pentylamine, 1-hexanamine, 1-heptanamine, 1-octanamine, 1-nonanamine, 1-decanamine, 1-isopropylamine, triethyleneamine, 3-methoxypropylamine, 3-ethoxypropylamine, 3-isopropoxy-1-propanamine, 3-propyl-1-propanamine, 3-butoxy-1-propanamine, 1,4-dioxa-1-ethoxyamine, 4,4-dimethoxybutylamine, 4,4-diethoxy-1-butanamine, 2-methoxyethanamine, 3-ethoxyethanamine, 3-isopropoxy-1-ethoxyethanamine, 4,4-dimethoxyethylamine, 4,4-diethoxy-1-ethylamine, tetrahydro-2-furanylmethylamine, 2-phenoxyethanamine, 2-(3,4-dimethoxyphenyl)ethanamine, 2-(2,5-dimethoxyphenyl)ethylamine, 1,2,2,-trimethyl-1-propanamine, 2-methyl-1-butanamine, 3-methyl-1-butanamine, 1,3-dimethyl-1-butanamine, 4-methyl-1-pentanamine, 3,3-dimethyl-1-butanamine, 1,4-dimethyl-1-pentanamine, 1-methyl-1- hexanamine, 1-methyl-1-heptanamine, 2-ethyl-1-hexanamine, 2-aminoethanol, 3-amino-1-propanol, (2R)-1-amino-2-propanol, (2S)-1-amino-2-propanol, 2-amino-1-propanol, (2S)-1-amino-2-propanol, 2-amino-1,3-propanediol, 2-amino-2-methyl-1,3-propanediol, 2-amino-2-methyl-1-propanol, 4-amino-1-butanol, 2-amino-1-propanol, 2-ethylamino-1-butanol, 2-(2-aminoethoxy)ethanol, 5-amino-1-pentanol, 3-amino-2,2-dimethyl-1-propanol, 2-amino-2-ethyl-1,3-propanediol, 2-amino-3-methyl-1-butanol, 6-amino-1-hexanol, (1-aminocyclopentyl)methanol, 4-aminocyclohexanol, 2-aminocyclohexanol, 2-methyl-1-propanamine, cyclobutanamine, cyclopropylmethylamine, cyclopentanamine, cyclohexanamine, cyclohexanmethylamine, adamantanemethylamine, Si-methyl-diethoxy-propylamine, Si-trithoxy-propylamine, 1,4-diazepane, N,N'-diethyl-1,2-ethanediamine, N,N'-diisopropyl-1,2-ethanediamine, N,N'-dimethyl-1,2-propanediamine, N,N'-dimethyl-1,3-propanediamine, N,N'-diethyl-1,3-propanediamine, N,N'-diethyl-1,4-pentanediamine, N,N'-bis(2-hydroxyethyl)ethylenediamine, N,N'-bis(2-hydroxyethyl)propylenediamine, and mixtures thereof; and the secondary amine compound is selected from the group consisting of 4,4'-trimethylenepiperidine, N,N'-dimethylethylenediamine, piperazine, 2-methylpiperazine, 3-methyl-4-(3-methylphenyl)piperazine, 3-methylpiperazine, 4-(phenylmethyl)piperazine, 4-(1-phenylethyl)piperazine, 4-(1,1'-dimethoxycarbonyl)piperazine, 4-(2-(bis(2-propenyl)amino)ethyl)piperazine, 1-(2-aminoethyl)piperazine, 4-(aminomethyl)piperazine, N,N'-dimethyl-1,2-ethanediamine, N,N'-diethyl-1,2-ethanediamine, N,N'-diisopropyl-1,2-ethanediamine, N,N'-dimethyl-1,2-propyldiamine, N,N'-diethyl-1,2-propyldiamine, N,N'-diisopropyl-1,2-propyldiamine, N,N'-dimethyl-1,2-hexanediamine, N,N'-dimethyl-N-[3-(methylamino)propyl]-1,3-propanediamine, N-[2-(methylamino)ethoxyethyl]-N,N'-dimethylamine, N-[2-(methylamino)dioxyethyl]-N,N'-dimethylamine, 1,4-diazepane, and mixtures thereof.

In an embodiment, the heterocyclic alkyl amine compound is selected from the group consisting of 1-(3-aminopropyl)imidazole (API), 1-(2-aminoethyl)pyrrolidine, 2-(2-aminoethyl)-1-methylpyrrolidine, 1-(2-aminoethyl)piperidine, N-(3-aminopropyl)-2-pipecoline, N-(N-methyl-N-benzene)-1-propylamine, N-(3-aminopropyl)-2-pyrrolidinone, 2-(2-pyridyl)ethylamine, 4-(2-aminoethyl)morpholine, 3-morpholinopropylamine, histidine, and mixtures thereof.

In an embodiment, the pH-sensitive block copolymer has a molecular weight of 1,000 to 20,000 g/mol.

According to another aspect of the present invention, there is provided a drug or protein carrier using the pH-sensitive block copolymer, comprising: a hydrophilic block derived from the polyethylene glycol compound; a hydrophobic block derived from the poly(amino acid) compound; and tertiary amine groups ionizable at pH 6.0~7.0 between the two blocks, wherein the pH-sensitive block copolymer forms micelles in the pH range of 7.0-7.4 by reversible self-assembly, the heterocyclic alkyl amine compound induces the formation of polyionic complexes with the micelles, and the polyionic complexes stably contain a drug or protein during circulation along blood vessels of a human body and release the drug or protein at a disease site.

In an embodiment, the drug or protein is an anticancer agent selected from the group consisting of human serum albumin (HSA), paclitaxel, doxorubicin, retinoic acids, cisplatin, camptothecin, fluorouracil (5-FU), docetaxel, tamoxifen, anasterozole, carboplatin, topotecan, belotecan, irinotecan, gleevec and vincristine, an anti-inflammatory agent selected from the group consisting of aspirin, salicylates, ibuprofen, naproxen, fenoprofen, indomethacin, phenyltazone, methotrexate, cyclophosphamide, mechlorethamine, dexamethasone, prednisolone, celecoxib, valdecoxib, nimesulide, cortisone and corticosteroid, or a mixture thereof; and is released when the micelle particles collapse locally at pH<7.0 at a cancer or inflammatory disease site.

In an embodiment, the cancer disease is breast cancer, lung cancer, uterine cancer, cervical cancer, prostate cancer, pharyngeal cancer, pancreatic cancer, brain tumor, liver cancer, skin cancer, esophageal cancer, testicular cancer, renal cancer, colorectal cancer, thyroid cancer, tongue cancer or rectal cancer.

In an embodiment, the inflammatory disease is rheumatoid arthritis, osteoarthritis or arteriosclerosis.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
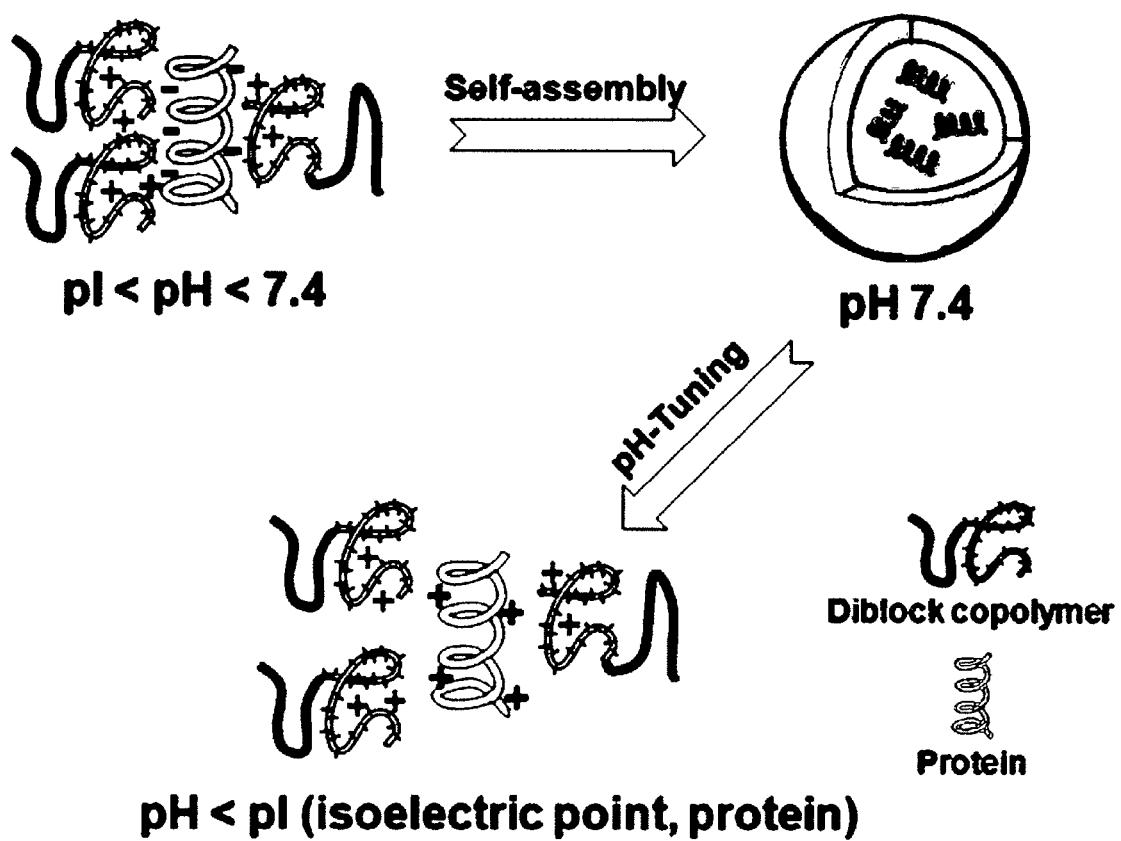
FIG. 1 shows schematic diagrams in which a block copolymer of a polyethylene glycol compound and a poly(β-amino ester) compound is self-assembled at a pH higher than the isoelectric point (pI) of protein but lower than 7.4 to form polyionic complex micelles capable of stably containing the protein and releasing the protein at a pH lower than the isoelectric point (pI) by charge repulsion between the block copolymer and the protein.
Figure 2:
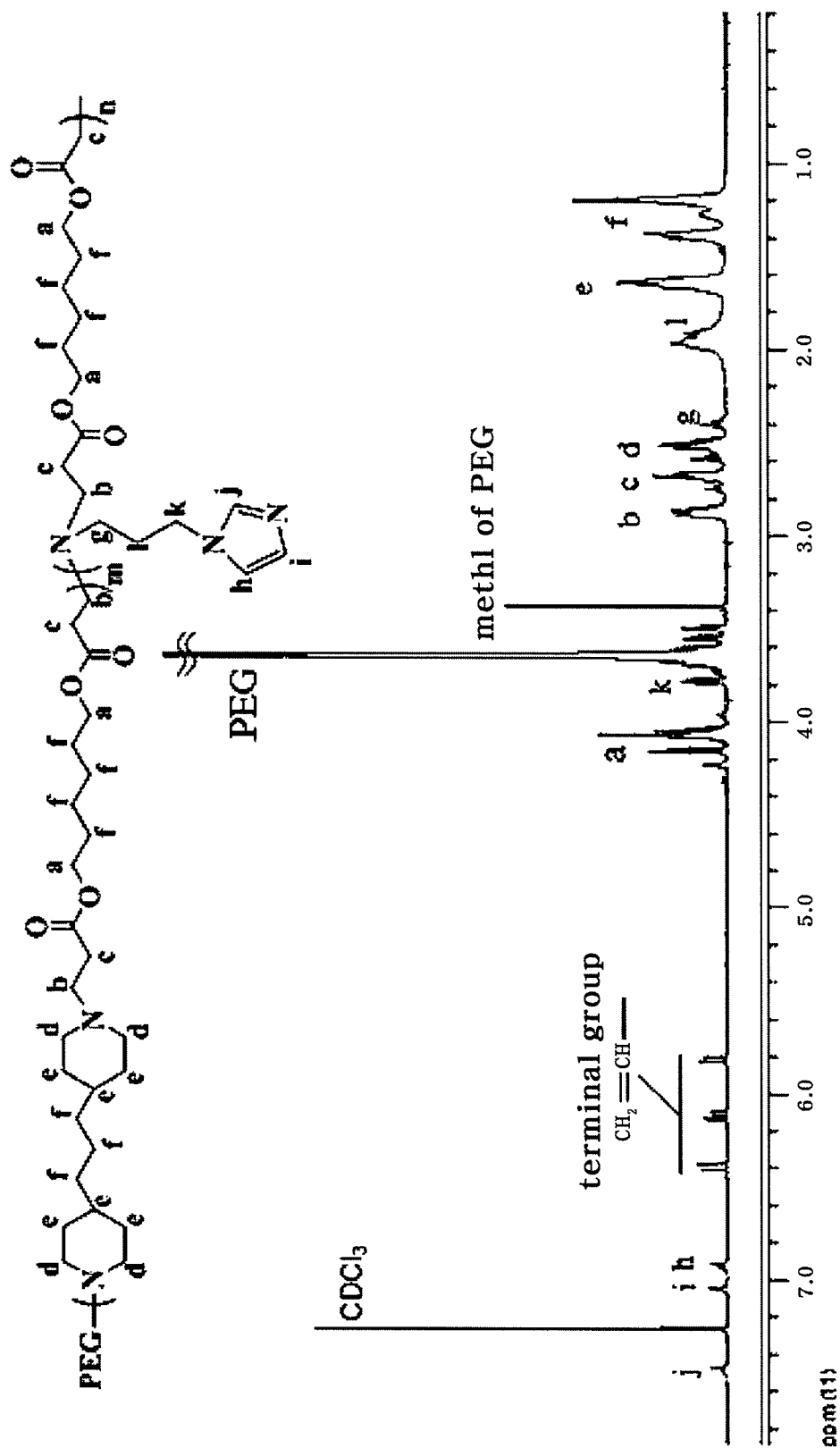
FIG. 2 is one of the $^1$H-NMR spectra of pH-sensitive block copolymers prepared using a polyethylene glycol compound and a poly(β-amino ester) compound in Examples 1 to 3.
Figure 3:
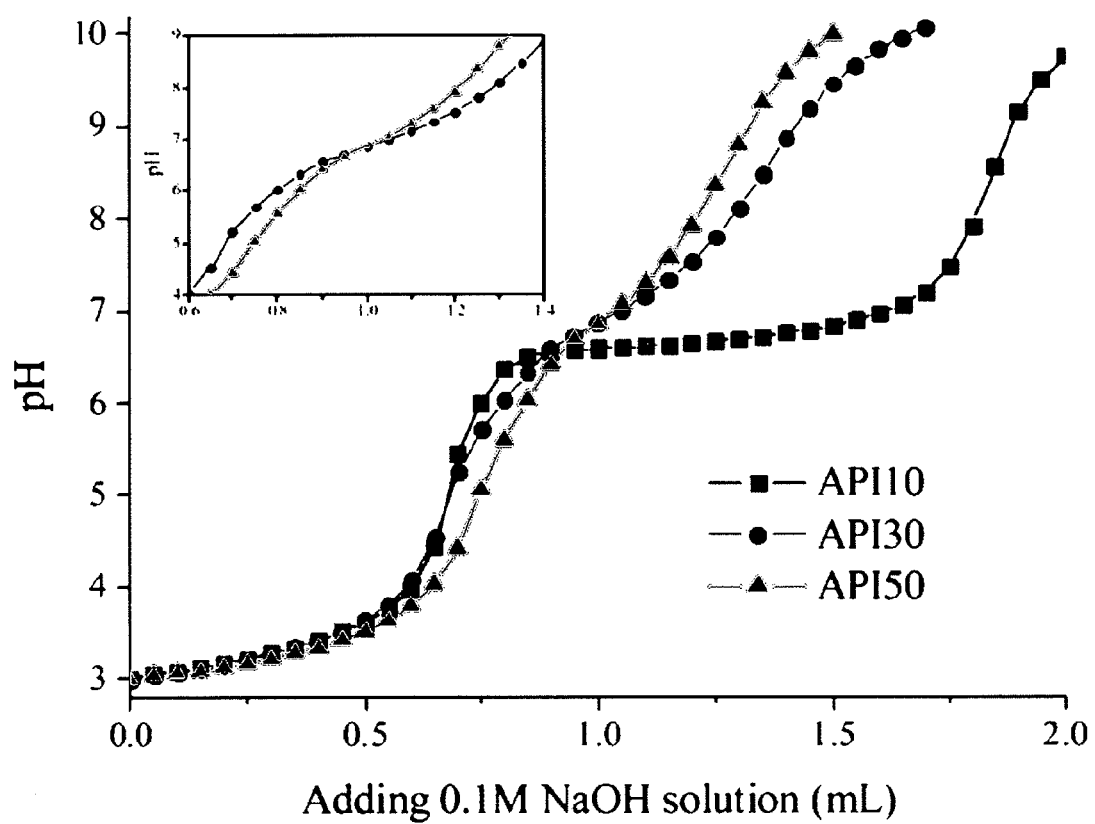
FIG. 3 is a graph showing acid-base titration profiles depending on changes in the aminopropylimidazole (API) content of pH-sensitive block copolymers prepared in Examples 1 to 3: (■) PEG-PAE-API10 (API10), (●) PEG-PAE-API30 (API30), (▲) PEG-PAE-API50 (API50)

Exemplary embodiments of the present invention will now be described in detail with reference to the accompanying drawings. It should be noted that whenever possible, the same reference numerals will be used throughout the drawings and the description to refer to the same or like parts. In describing the present invention, detailed descriptions of related known functions or configurations are omitted in order not to obscure the essential subject of the invention unclear.

As used herein, the terms "about", "substantially", etc. are intended to allow some leeway in mathematical exactness to account for tolerances that are acceptable in the trade and to prevent any unconscientious violator from unduly taking advantage of the disclosure in which exact or absolute numerical values are given so as to help understand the invention.

The present invention provides a block copolymer prepared by copolymerization of a pH-sensitive poly(amino acid) compound, such as a poly(β-amino ester), a poly(β-amido amine) or a copolymer thereof, a hydrophilic polyethylene glycol compound and a heterocyclic alkyl amine compound capable of forming strong ionic complexes. Therefore, the block copolymer of the present invention is sensitive to pH variations in the body and can form a micelle structure in a particular pH region. In addition, the micelles stably retain a drug or protein contained therein and can efficiently release the drug or protein in response to pH variations at a disease site. Specifically, the pH-sensitive block copolymer of the present invention is self-assembled at a pH higher than the isoelectric point (pI) of protein but lower than 7.4 to form nano-sized polyionic complex micelles having a core-shell structure capable of stably containing a drug or protein. The micelles release the drug or protein at a pH lower than the isoelectric point (pI) by charge repulsion between the block copolymer and the drug or protein.

The polyionic complex micelles stably contain a drug or protein in a particular pH range, for example, pH 7.0~7.4, which corresponds to the pH range of normal cells in the body, but their structure collapses at pH<7.0, which can be found in abnormal cells, such as cancer cells. These pH characteristics enable the use of the polyionic complex micelles as carriers for the delivery of a drug or protein to particular targets such as cancer cells.

More specifically, the degree of ionization of tertiary amine groups present in a poly(β-amino ester) (PAE), a poly(β-amido amine)(PAA) or a copolymer thereof (PAEA) as the poly(amino acid) compound increases at a low pH (<7.0), rendering the poly(amino acid) compound soluble in water as a whole. This water solubility makes it impossible to form micelles. In the meantime, the degree of ionization of the poly(amino acid) compound is lowered at pH 7.0~7.4, rendering the poly(amino acid) compound hydrophobic. This hydrophobicity enables the formation of micelles by self-assembly. The tertiary amine groups of the heterocyclic alkyl amine compound in the backbone of the block copolymer form strong polyionic complexes with a drug or protein. The polyionic complexes stably contain without releasing the drug or protein, stably circulate along blood vessels of a human body, and release the drug or protein in response to pH variations at a disease site, such as a cancer tissue. That is, the polyionic complex micelles can act as target-specific drug or protein carriers.

In addition, the block copolymer capable of forming pH-sensitive micelles can deliver therapeutic genes and agents. Furthermore, the block copolymer of the present invention can find application in various fields. For example, the block copolymer of the present invention can be used for diagnostic imaging because it can deliver diagnostic substances to abnormal cells.

For use in various applications, including genetic variation, the micelles targeting cancer cells, which are formed at pH 7.0-7.4 and collapse at pH<7.0, can be designed by appropriately varying the kind, molar ratio and molecular weight of the components constituting the block copolymer and/or the kind of the functional groups in the blocks.

The conditions for the formation of the pH-sensitive block copolymer, for example, the kind, molar ratio and molecular weight of the components constituting the block copolymer and/or the kind of the functional groups in the blocks, can be varied to easily control the biodegradation rate of the pH-sensitive block copolymer micelles in the body, enabling the delivery of a drug to a desired position in a target specific manner.

The polyethylene glycol compound constituting the block copolymer of the present invention may be any of the hydrophilic biodegradable compounds known in the art.

As the polyethylene glycol compound, particularly preferred is a compound represented by Formula 1:

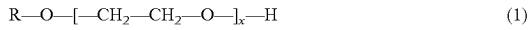

wherein R is a hydrogen atom or a $C_1$-$C_6$ alkyl group and x is a natural number ranging from 1 to 200.

The alkyl group in Formula 1 means a linear or branched lower saturated aliphatic hydrocarbon, and examples thereof include methyl, ethyl, n-propyl, isopropyl, n-butyl, s-butyl, isobutyl, t-butyl and n-pentyl groups.

More preferably, the polyethylene glycol compound has a monofunctional group, such as an acrylate or methacrylate group, at one end thereof.

For example, the polyethylene glycol compound end-capped with an acrylate group is can be represented by Formula 2:

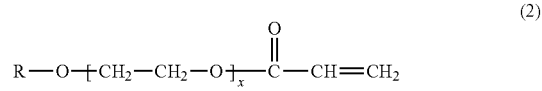

wherein R is a hydrogen atom or a $C_1$-$C_6$ alkyl group and x is a natural number ranging from 1 to 200.

The alkyl group in Formula 2 means a linear or branched lower saturated aliphatic hydrocarbon, and examples thereof include methyl, ethyl, n-propyl, isopropyl, n-butyl, s-butyl, isobutyl, t-butyl and n-pentyl groups.

The polyethylene glycol compound has a number average molecular weight ($M_n$) of 500 to 5,000 g/mol but is not particularly limited to this range. Out of this range, i.e. if the polyethylene glycol compound has a number average molecular weight ($M_n$) higher than 5,000 g/mol or lower than 500 g/mol, it is difficult to control the molecular weight of the final block copolymer and to form micelles using the block copolymer. Specifically, if the number average molecular weight of the polyethylene glycol compound is less than 500 g/mol, the hydrophilic block is too short in length to induce self-assembly of the block copolymer resulting from the hydrophilic/hydrophobic balance at a particular pH, making it difficult to form micelles. Although formed, the micelles are dissolved in water and are liable to collapse. Meanwhile, if the number average molecular weight of the polyethylene glycol compound exceeds 5,000 g/mol, the length of the corresponding block is too long compared to the molecular weight of the hydrophobic poly(amino acid) compound, causing hydrophilic/hydrophobic imbalance. As a result, the block copolymer does not form micelles at a particular pH and may precipitate.

The poly(amino acid) compound constituting the block copolymer of the present invention has both hydrophobicity and pH-sensitivity, and non-limiting examples thereof include poly(β-amino ester) (PAE), poly(amido amine) (PAA) and a copolymer thereof (poly(β-amino ester)-(amido amine, PAEA).

The water solubility of the poly(amino acid) compounds, i.e. PAE, PAA and PAEA, are dependent on pH due to the presence of tertiary amine groups therein. Due to the ionization characteristics, a micelle structure of the poly(amino acid) compounds may be formed or collapse depending on pH variations in the body. The poly(amino acid) compound can be prepared by any methods known in the art. In an embodiment, a bisacrylate or bisacrylamide compound having at least one double bond is polymerized with an amine compound by the Michael reaction to prepare the poly(amino acid) compound.

The bisacrylate compound can be represented by Formula 3:

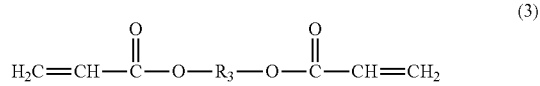

(3)

wherein $R_3$ is a $C_1$-$C_{10}$ alkyl group.

Non-limiting examples of suitable bisacrylate compounds for use in the present invention include ethylene glycol diacrylate, 1,4-butanediol diacrylate, 1,3-butanediol diacrylate, 1,6-hexanediol diacrylate, 1,5-pentanediol diacrylate, 2,5-pentanediol diacrylate, 1,6-hexanediol ethoxylate diacrylate, 1,6-hexanediol propoxylate diacrylate, 3-hydroxy-2,2-dimethylpropyl-3-hydroxy-2,2-dimethylpropionate diacrylate, 1,7-heptanediol diacrylate, 1,8-octanediol diacrylate, 1,9-nonanediol diacrylate, 1,10-decanediol diacrylate, and mixtures thereof.

The bisacrylamide compound can be represented by Formula 4:

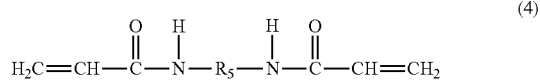

(4)

wherein $R_5$ is a $C_1$-$C_{10}$ alkyl group.

Non-limiting examples of suitable bisacrylamide compounds for use in the present invention include N,N'-methylene bisacrylamide (MDA), N,N'-ethylene bisacrylamide and mixtures thereof.

The amine compound may be any compound having at least one amine group.

As the amine compound, particularly preferred is a primary amine compound represented by Formula 5:

$R_1$—$NH_2$ (5)

wherein $R_1$ is a $C_1$-$C_{10}$ alkyl group;
a secondary amine represented by Formula 6:

(6)

wherein $R_1$ and $R_2$ are each independently a $C_1$-$C_{10}$ alkyl group; or
a mixture thereof.

Non-limiting examples of suitable primary amine compounds for use in the present invention include 1-methylamine, 1-ethylamine, 1-propylamine, 1-butylamine, 1-pentylamine, 1-hexanamine, 1-heptanamine, 1-octanamine, 1-nonanamine, 1-decanamine, 1-isopropylamine, triethyleneamine, 3-methoxypropylamine, 3-ethoxypropylamine, 3-isopropoxy-1-propanamine, 3-propyl-1-propanamine, 3-butoxy-1-propanamine, 1,4-dioxa-1-ethoxyamine, 4,4-dimethoxybutylamine, 4,4-diethoxy-1-butanamine, 2-methoxyethanamine, 3-ethoxyethanamine, 3-isopropoxy-1-ethoxyethanamine, 4,4-dimethoxyethylamine, 4,4-diethoxy-1-ethylamine, tetrahydro-2-furanylmethylamine, 2-phenoxyethanamine, 2-(3,4-dimethoxyphenyl)ethanamine, 2-(2,5-dimethoxyphenyl)ethylamine, 1,2,2,-trimethyl-1-propanamine, 2-methyl-1-butanamine, 3-methyl-1-butanamine, 1,3-dimethyl-1-butanamine, 4-methyl-1-pentanamine, 3,3-dimethyl-1-butanamine, 1,4-dimethyl-1-pentanamine, 1-methyl-1-hexanamine, 1-methyl-1-heptanamine, 2-ethyl-1-hexanamine, 2-aminoethanol, 3-amino-1-propanol, (2R)-1-amino-2-propanol, (2S)-1-amino-2-propanol, 2-amino-1-propanol, (2S)-1-amino-2-propanol, 2-amino-1,3-propanediol, 2-amino-2-methyl-1,3-propanediol, 2-amino-2-methyl-1-propanol, 4-amino-1-butanol, 2-amino-1-propanol, 2-ethylamino-1-butanol, 2-(2-aminoethoxy)ethanol, 5-amino-1-pentanol, 3-amino-2,2-dimethyl-1-propanol, 2-amino-2-ethyl-1,3-propanediol, 2-amino-3-methyl-1-butanol, 6-amino-1-hexanol, (1-aminocyclopentyl)methanol, 4-aminocyclohexanol, 2-aminocyclohexanol, 2-methyl-1-propanamine, cyclobutanamine, cyclopropylmethylamine, cyclopentanamine, cyclohexanamine, cyclohexanmethylamine, adamantane-methylamine, Si-methyl-diethoxy-propylamine, Si-trithoxy-propylamine, 1,4-diazepane, N,N'-diethyl-1,2-ethanediamine, N,N'-diisopropyl-1,2-ethanediamine, N,N'-dimethyl-1,2-propanediamine, N,N'-dimethyl-1,3-propanediamine, N,N'-diethyl-1,3-propanediamine, N,N'-diethyl-1,4-pentanediamine, N,N'-bis(2-hydroxyethyl)ethylenediamine, N,N'-bis(2-hydroxyethyl)propylenediamine, and mixtures thereof.

Non-limiting examples of suitable secondary amine compounds for use in the present invention include 4,4'-trimethylenepiperidine, N,N'-dimethylethylenediamine, piperazine, 2-methylpiperazine, 3-methyl-4-(3-methylphenyl)piperazine, 3-methylpiperazine, 4-(phenylmethyl)piperazine, 4-(1-phenylethyl)piperazine, 4-(1,1'-dimethoxycarbonyl)piperazine, 4-(2-(bis(2-propenyl)amino)ethyl)piperazine, 1-(2-aminoethyl)piperazine, 4-(aminomethyl)piperazine, N,N'-dimethyl-1,2-ethanediamine, N,N'-diethyl-1,2-ethanediamine, N,N'-diisopropyl-1,2-ethanediamine, N,N'-dimethyl-1,2-propyldiamine, N,N'-diethyl-1,2- propyldiamine, N,N'-diisopropyl-1,2-propyldiamine, N,N'-dimethyl-1,2-hexanediamine, N,N'-dimethyl-N-[3-(methylamino)propyl]-1,3-propanediamine, N-[2-(methylamino)ethoxyethyl]-N,N'-dimethylamine, N-[2-(methylamino)dioxyethyl]-N,N'-dimethylamine, 1,4-diazepane, and mixtures thereof.

On the other hand, the heterocyclic alkyl amine compound is used to easily induce the formation of polyionic complexes with a drug. The heterocyclic alkyl amine compound may be any compound that has at least amine group and at least one tertiary amine group on the aromatic ring thereof. As the heterocyclic alkyl amine compound, particularly preferred is a compound represented by Formula 7:

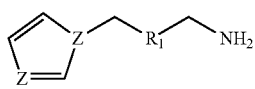
(7)

wherein $R_1$ is a $C_1$-$C_6$ alkyl group.

The alkyl group in Formula 7 means a linear or branched lower saturated aliphatic hydrocarbon, and examples thereof include methyl, ethyl, n-propyl, isopropyl, n-butyl, s-butyl, isobutyl, t-butyl and n-pentyl groups. A representative example of the heterocyclic alkyl amine compound is 1-(3-aminopropyl)imidazole (API). In addition to such aminoalkylimidazole compounds, other examples are 1-(2-aminoethyl)pyrrolidine, 2-(2-aminoethyl)-1-methylpyrrolidine, 1-(2-aminoethyl)piperidine, N-(3-aminopropyl)-2-pipecoline, N-(N-methyl-N-benzene)-1-propylamine, N-(3-aminopropyl)-2-pyrrolidinone, 2-(2-pyridyl)ethylamine, 4-(2-aminoethyl)morpholine, 3-morpholinopropylamine, histidine, and mixtures thereof. These compounds can also induce the formation of strong ionic complexes with a drug or protein.

The reaction molar ratio of the bisacrylate or bisacrylamide compound to the amine compound for the preparation of the pH-sensitive poly(amino acid) compound, for example, PAE, PAA or PAEA, is preferably in the range of 0.5:1 to 2.0:1. Out of this range, it is difficult to form micelles because the resulting polymer has a limited molecular weight of 1,000 or less.

The pH-sensitive block copolymer of the present invention, which is prepared by copolymerization of the polyethylene glycol compound, the poly(amino acid) compound and the heterocyclic alkyl amine compound, can be represented by Formulas 8 to 10:

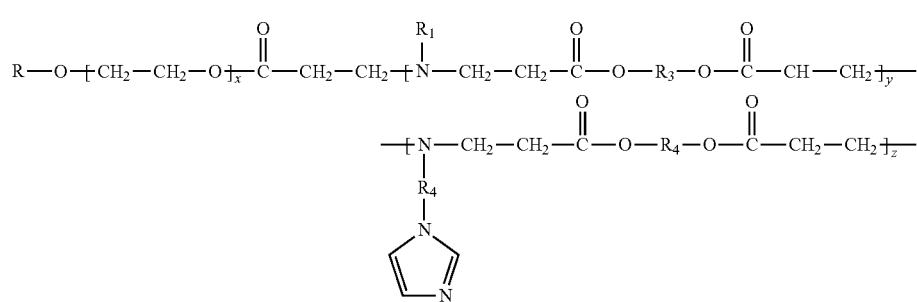
(8)

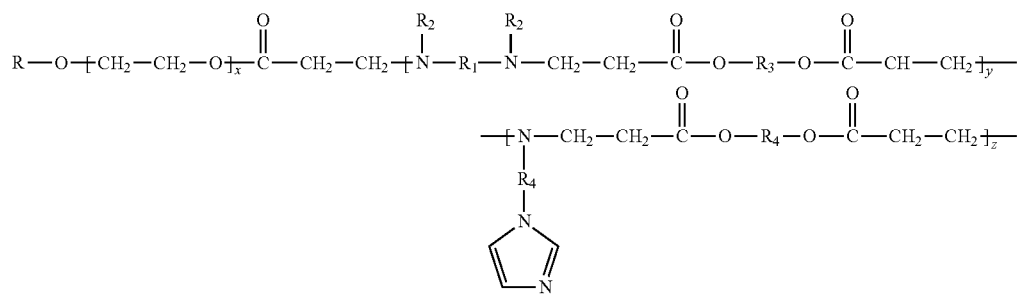
(9)

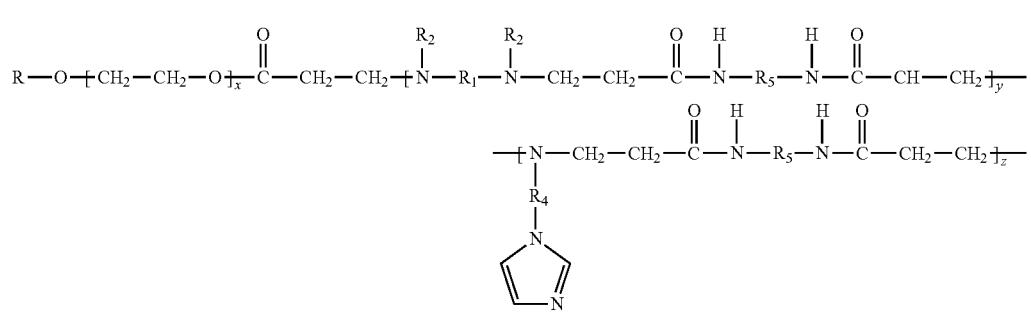
(10)

wherein R is a hydrogen atom or a $C_1$-$C_6$ alkyl group, x is a natural number from 1 to 200, $R_1$, $R_3$ and $R_4$ are each independently a $C_1$-$C_{10}$ alkyl group, and y and z are each independently a natural number from 1 to 100.

Micelles of the block copolymer of Formula 8 may be formed or collapse depending on pH variations because of the amphiphilicity and pH sensitivity of the block copolymer. It is preferred that the block copolymer of Formula 8 forms micelles in the pH range of 7.0 to 7.4 and the micelles collapse in the pH range of 6.5 to 7.0. Particularly, the block copolymer of the present invention is highly sensitive to pH within ±0.2. Due to this advantage, the block copolymer of the present invention can give satisfactory results when it is used in applications (for example, carriers for drug release or diagnosis) requiring sensitivity depending on pH variations in the body. Particularly, the heterocyclic alkyl amine compound, which induces the micelles to stably contain a drug or protein therein, allows the block copolymer of the present invention to provide a target-specific drug or protein carrier that stably contains the drug or protein when injected to a human body through a blood vessel, circulates along the blood vessels of the human body and can release the drug or protein in response to pH variations at a disease site.

So long as the block copolymer of the present invention maintains its pH sensitivity and physical properties to form micelles, it may further comprise at least one structural unit known in the art, in addition to the hydrophilic polyethylene glycol compound, the heterocyclic alkyl amine compound and the poly(amino acid) compound. The block copolymer comprising the additional structural unit is encompassed within the scope of the present invention.

There is no particular restriction on the molecular weight of the block copolymer. Preferably, the block copolymer of the present invention has a molecular weight of 1,000 to 20,000 g/mol. The block copolymer having a molecular weight of less than 1,000 g/mol is difficult to form micelles at a particular pH. Although formed, the micelles are dissolved in water and are liable to collapse. Meanwhile, the block copolymer having a molecular weight exceeding 20,000 g/mol causes hydrophilic/hydrophobic imbalance. As a result, the block copolymer does not form micelles at a particular pH and may precipitate.

There is no particular restriction on the content of the polyethylene glycol block in the pH-sensitive block copolymer. The polyethylene glycol block is present in an amount of 5 to 95 parts by weight and preferably 10 to 40 parts by weight, based on 100 parts of the pH-sensitive block copolymer. The presence of the polyethylene glycol block in an amount of less than 5 parts by weight may cause precipitation of the block copolymer without forming micelles. Meanwhile, the presence of the polyethylene glycol block in an amount exceeding 95 parts by weight leads to too small a number of blocks present within micelles and causes the block copolymer to remain dissolved. Further, the reaction molar ratio between the polyethylene glycol compound and the poly(amino acid) compound, for example, PAE, PAA or PAEA, can be appropriately controlled to form various multi-block structures, for example, AB type diblock structures, and ABA and BAB type tri-block structures, and higher.

The pH-sensitive block copolymer of the present invention can be prepared by suitable methods known in the art. First, an acrylate group is introduced into a PEG compound by Reaction 1:

Reaction 1

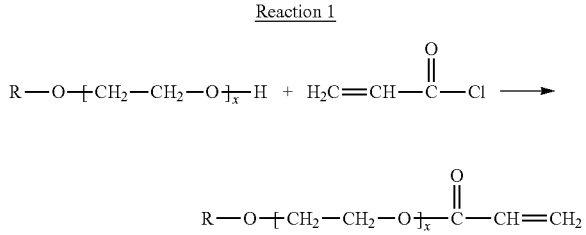

wherein R is a hydrogen atom or a $C_1$-$C_6$ alkyl group and x is a natural number from 1 to 200.

As depicted in Reaction 1, the PEG compound reacts with acryloyl chloride to give an acrylate-polyethylene glycol (A-PEG) having a double bond at one end thereof.

The pH-sensitive block copolymer of the present invention may be synthesized by Reaction 2:

Reaction 2

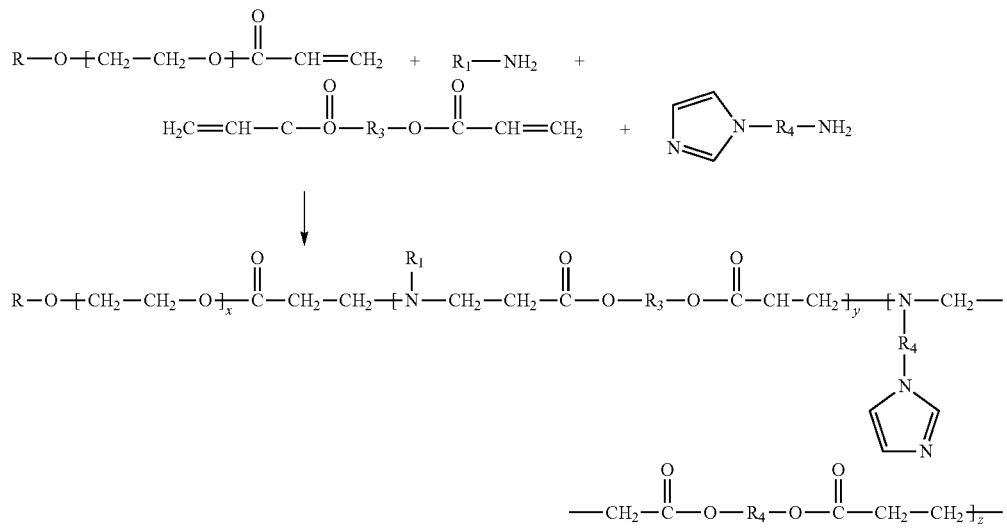

wherein R is a hydrogen atom or a $C_1$-$C_6$ alkyl group, x is a natural number from 1 to 200, $R_1$, $R_3$ and $R_4$ are each independently a $C_1$-$C_{10}$ alkyl group, and y and z are each independently a natural number from 1 to 100.

As depicted in Reaction 2, the polyethylene glycol compound (A-PEG) having a terminal acrylate group, a primary amine, a bisacrylate and an aminoalkylimidazole are copolymerized by a reaction known in the art. The Michael reaction of the primary amine and the bisacrylate gives a poly(β-amino ester). Thereafter, the poly(β-amino ester) is copolymerized with the polyethylene glycol compound having a terminal acrylate group and the heterocyclic alkyl amine compound, affording the final block copolymer. Organic solvents suitable for use in the preparation of the block copolymer are toluene, chloroform, tetrahydrofuran, dimethyl sulfoxide, dimethylformamide and methylene chloride.

Alternatively, the pH-sensitive block copolymer of the present invention may be synthesized by Reaction 3:

Reaction 3

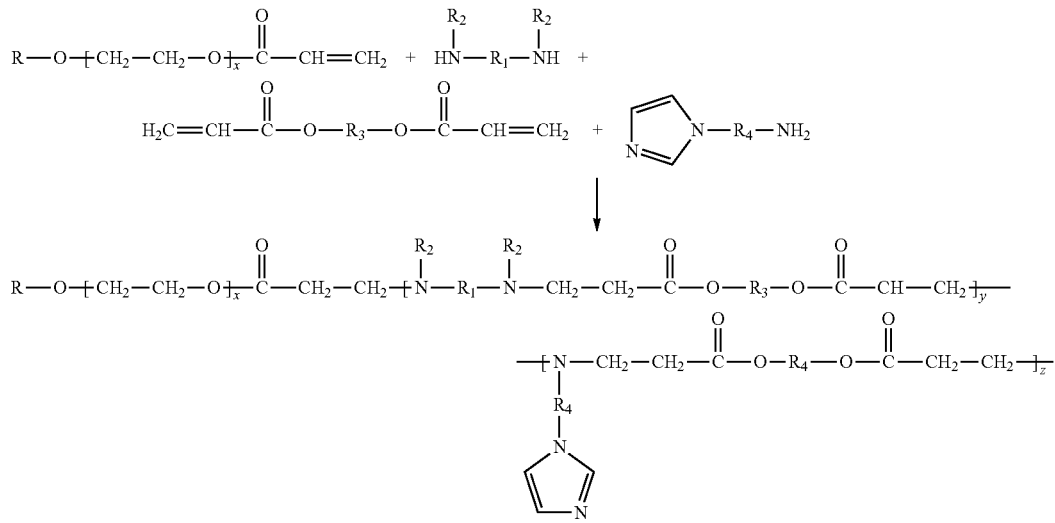

wherein R is a hydrogen atom or a $C_1$-$C_6$ alkyl group, x is a natural number from 1 to 200, $R_1$, $R_2$, $R_3$ and $R_4$ are each independently a $C_1$-$C_{10}$ alkyl group, and y and z are each independently a natural number from 1 to 100.

As depicted in Reaction 3, the polyethylene glycol compound (A-PEG) having a terminal acrylate group, a secondary amine, a bisacrylate and a heterocyclic alkyl amine compound are copolymerized by a reaction known in the art. The Michael reaction of the secondary amine and the bisacrylate gives a poly(β-amino ester). Thereafter, the poly(β-amino ester) is copolymerized with the polyethylene glycol compound having a terminal acrylate group and the heterocyclic alkyl amine compound, affording the final block copolymer. Organic solvents suitable for use in the preparation of the block copolymer are toluene, chloroform, tetrahydrofuran, dimethyl sulfoxide, dimethylformamide and methylene chloride.

Alternatively, the pH-sensitive block copolymer of the present invention may be synthesized by Reaction 4:

Reaction 4

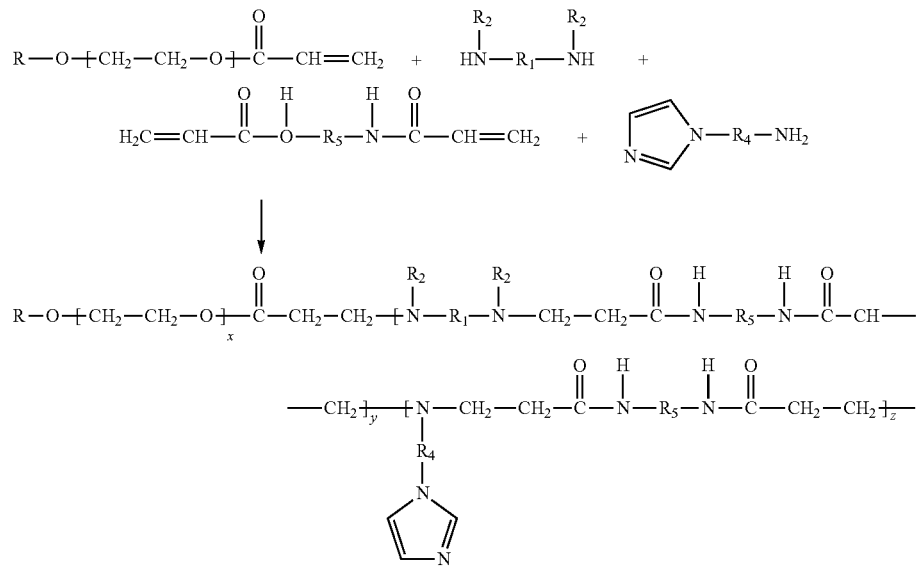

wherein R is a hydrogen atom or a $C_1$-$C_6$ alkyl group, x is a natural number from 1 to 200, $R_1$, $R_2$, $R_4$ and $R_5$ are each independently a $C_1$-$C_{10}$ alkyl group, and y and z are each independently a natural number from 1 to 100.

As depicted in Reaction 4, the polyethylene glycol compound (A-PEG) having a terminal acrylate group, a primary or secondary amine, a bisacrylamide and a heterocyclic alkyl amine compound are copolymerized by a reaction known in the art. The Michael reaction of the primary or secondary amine and the bisacrylamide gives a poly(β-amido amine) as a poly(amino acid). Thereafter, the poly(β-amido amine) is copolymerized with the polyethylene glycol compound having a terminal acrylate group and the heterocyclic alkyl amine compound, affording the final pH-sensitive block copolymer. Organic solvents suitable for use in the preparation of the block copolymer are toluene, chloroform, tetrahydrofuran, dimethyl sulfoxide, dimethylformamide and methylene chloride.

On the other hand, the heterocyclic alkyl amine compound is added during the copolymerization to induce the formation of ionic complexes of the micelles and a drug or protein. In the Examples Section, $^1$H-NMR spectroscopy and gel permeation chromatography (GPC) were performed on the block copolymer to confirm efficient incorporation of the heterocyclic alkyl amine compound into the copolymer. A fluorescence spectrometer and a dynamic light scattering (DLS) analyzer were used to measure changes in the concentration and size of the micelles with varying pH values. The zeta potential values of the micelles and a drug or protein were measured at various pH values and were compared to predict the degree of formation of ionic complexes of the micelles and the drug or protein. Changes in the particle size of the micelles with time were measured by DLS to evaluate the stability of a drug or protein contained in the micelles. Electrophoresis experiments were conducted to compare and analyze the ability to form ionic complexes.

Based on the above analytical results, it was intended to identify the applicability of the micelles to drug or protein carriers. To this end, the present inventors have prepared micelles of the block copolymer prepared in Example 3 and human serum albumin (HSA) as a model drug contained in the block copolymer. The release behavior of the HSA from the micelles at various pH values was investigated by circular dichroism (CD). In actuality, after the micelles and the HSA-containing micelles were labeled with FITC as a fluorescent marker, the fluorescence labeling performance of incubated MDA-MB-435 cells as breast cancer cell lines and the degree of release of the HSA were observed by confocal microscopy. MTT assay for determining the growth of the MDA-MB-435 cells was conducted to evaluate the cytotoxicity of the HSA-containing micelles.

The present invention also provides a polymeric micelle-type drug composition comprising (a) the block copolymer forming micelles in response to pH variations and (b) a physiologically active drug or protein filled in the block copolymer.

When the polymeric micelle-type drug composition of the present invention is injected into the body, it forms micelles and strong ionic complexes with the physiologically active drug or protein without releasing the drug or protein at the initial stage of the injection. The micelles stably contain the drug or protein and collapse to release the drug or protein when they reach disease sites, such as cancer cells, having a locally low pH, enabling target-specific delivery of the drug or protein.

There is no particular restriction on the kind of the physiologically active drug or protein filled in the block copolymer. The physiologically active drug or protein may be an anticancer agent, an anti-inflammatory agent, an antiviral agent, an anesthetic agent, an antiemetic agent, an anti-histamine agent, or a mixture thereof. Non-limiting examples of suitable anticancer agents for use in the present invention include human serum albumin (HSA), paclitaxel, doxorubicin, retinoic acids, cis-platin, camptothecin, fluorouracil (5-FU), docetaxel, tamoxifen, anasterozole, carboplatin, topotecan, belotecan, irinotecan, gleevec and vincristine. Non-limiting examples of suitable anti-inflammatory agents for use in the present invention include aspirin, salicylates, ibuprofen, naproxen, fenoprofen, indomethacin, phenyltazone, methotrexate, cyclophosphamide, mechlorethamine, dexamethasone, prednisolone, celecoxib, valdecoxib, nimesulide, cortisone and corticosteroid.

The pH-sensitive drug or protein carrier containing the drug filled therein was designed in the molecular structure to keep its nanometer-sized particles and stably contain the drug without releasing the drug at pH 7.0~7.4, which is the pH range of normal cells in the body. In addition, the pH-sensitive drug or protein carrier was designed such that the particles collapse to release the drug at pH<7.0 which is a pH condition in abnormal cells such as cancer and inflammatory disease sites. In addition, the pH-sensitive drug or protein carrier was designed such that the particles are absorbed into cells and collapse in the endosome at pH≤6.0 by endocytosis to release the drug or protein.

The kind, molar ratio and molecular weight of the components constituting the block copolymer and the kind of the functional groups in the blocks can be appropriately varied to find utility of the block copolymer in other applications. For example, the target-specific micelles can be designed by labeling with folic acid, an RGD protein or an aptamer.

The polymeric micelle-type drug composition of the present invention may further comprise one or more additives selected from vehicles, stabilizers, pH-adjusting agents, antioxidants, preservatives, binders and disintegrating agents, which are commonly known in the art. The cancer disease may be breast cancer, lung cancer, uterine cancer, cervical cancer, prostate cancer, pharyngeal cancer, pancreatic cancer, brain tumor, liver cancer, skin cancer, esophageal cancer, testicular cancer, renal cancer, colorectal cancer, thyroid cancer, tongue cancer or rectal cancer. The inflammatory disease may be rheumatoid arthritis, osteoarthritis or arteriosclerosis.

The polyionic complex micelles can be formed by stirring, heating, ultrasonic scanning, solvent evaporation using emulsification, matrix formation, dialysis using an organic solvent, or a combination thereof.

The polyionic complex micelles have a diameter in the range of 10 to 200 nm but are not limited to this range. The polymeric micelle-type drug composition can be formulated into oral or parenteral preparation and can be provided in the form of an intravenously, intramuscularly or subcutaneously injectable preparation.

The present invention also provides use of the pH-sensitive block copolymer as a carrier for drug or protein delivery or disease diagnosis. The block copolymer may contain any material for the treatment, prevention or diagnosis of diseases.

The present invention also provides a method for preparing a pH-sensitive block copolymer capable of forming micelles, the method comprising copolymerizing (a) at least one compound selected from the group consisting of compounds containing an ester group, a tertiary amine group and a heterocyclic alkyl amine compound, and compounds containing an amide group, a tertiary amine group and a heterocyclic alkyl amine compound, or a copolymer thereof, and (b) a hydrophilic or amphiphilic compound.

The present invention will be explained in more detail with reference to the following examples and experimental examples. These examples are provided for illustrative purposes only and the present invention is not limited thereto.

EXAMPLES

Examples 1-10

Synthesis of pH-Sensitive Block Copolymers

Example 1

Preparation of Polyethylene glycol-poly(β-amino ester)-aminopropylimidazole Block Copolymer (PEG-PAE-API)

Polyethylene glycol methyl ether (MPEG5000, $M_n$=5,000) was dewatered in a vacuum oven at 90° C. for 2 hr and were then reacted with acryloyl chloride in toluene containing triethylamine (TEA) at 45° C. for 15 hr. The reaction mixture was filtered to remove unreacted triethylamine salt, extracted with a dilute aqueous hydrochloric acid solution, and precipitated in ethyl ether to afford polyethylene glycol end-capped with an acrylate group (A-PEG). A-PEG (0.1 mol), 4,4'-trimethylene dipiperidine (1 mol) as a diamine, 1,6-hexanediol diacrylate (1 mol) and aminopropylimidazole (0.1 mol) were placed in a two-neck round bottom flask and nitrogen gas was purged under reduced pressure. The reaction was continued in chloroform as a reaction solvent at 50° C. for 3 days. The reaction mixture was precipitated in hexane and ethyl ether (1:1) as co-solvent and dried, affording a polyethylene glycol-poly(β-amino ester)-aminopropylimidazole (PEG-PAE-API) block copolymer with a number average molecular weight ($M_n$) of 13,800 in a yield of 90%.

Example 2

A PEG-PAE-API block copolymer having a number average molecular weight ($M_n$) of 10,000 was prepared in a yield of 91% in the same manner as in Example 1, except that 4,4'-trimethylene dipiperidine and aminopropylimidazole (API) were used in amounts of 0.8 mol and 0.3 mol, respectively.

Example 3

A PEG-PAE-API block copolymer having a number average molecular weight ($M_n$) of 9,400 was prepared in a yield of 90% in the same manner as in Example 1, except that 4,4'-trimethylene dipiperidine and aminopropylimidazole (API) were used in amounts of 0.6 mol and 0.5 mol, respectively.

Example 4

A PEG-PAE-API block copolymer having a number average molecular weight ($M_n$) of 11,000 was prepared in a yield of 95% in the same manner as in Example 1, except that polyethylene glycol methyl ether (MPEG) having a molecular weight of 2,000 was used.

Example 5

A PEG-PAE-API block copolymer having a number average molecular weight ($M_n$) of 10,000 was prepared in a yield of 95% in the same manner as in Example 1, except that polyethylene glycol methyl ether (MPEG) having a molecular weight of 1,000 was used.

Example 6

A PEG-PAE-API block copolymer having a number average molecular weight ($M_n$) of 13,000 was prepared in a yield of 90% in the same manner as in Example 1, except that piperazine was used as a diamine instead of 4,4'-trimethylene dipiperidine.

Example 7

A PEG-PAE-API block copolymer having a number average molecular weight ($M_n$) of 12,500 was prepared in a yield of 93% in the same manner as in Example 1, except that 1,4-butanediol diacrylate was used instead of 1,6-hexanediol diacrylate.

Example 8

A PEG-PAEA-API block copolymer having a number average molecular weight ($M_n$) of 13,500 was prepared in a yield of 91% in the same manner as in Example 1, except that 0.5 mol of 4,4'-trimethylene dipiperidine and 0.5 mol of N,N-methylene bisacrylamide were used instead of 1 mol of 4,4'-trimethylene dipiperidine. This example was performed to control the biodegradation rate of the block copolymer.

Example 9

A PEG-PAEA-API block copolymer having a number average molecular weight ($M_n$) of 13,500 was prepared in a yield of 91% in the same manner as in Example 1, except that 0.5 mol of piperazine and 0.5 mol of N,N-methylene bisacrylamide were used instead of 1 mol of 4,4'-trimethylene dipiperidine. This example was performed to control the biodegradation rate of the block copolymer.

Example 10

A PEG-PAA-API block copolymer having a number average molecular weight ($M_n$) of 13,700 was prepared in a yield of 95% in the same manner as in Example 1, except that N,N'-methylene bisacrylamide was used instead of 1,6-hexanediol diacrylate.

Example 11

After 5% of human serum albumin (HSA) was contained in each of the PEG-PAE-API block copolymers prepared in Examples 1 to 3 to form micelles, the zeta potentials of the micelles and pure HSA were measured at various pH values. This example was performed to see the ability of the micelles to form ionic complexes with the protein.

Example 12

After 1 mol of HSA was contained in the PEG-PAE-API block copolymer prepared in Example 1 to form HSA-containing block copolymeric micelles ("API10"), the release behaviors of the HSA were compared at various pH values. This example was performed to see the ability of the micelles to release the HSA depending on the formation of the ionic complexes.

Example 13

After 3 mol of HSA was contained in the PEG-PAE-API block copolymer prepared in Example 2 to form HSA-containing block copolymeric micelles ("API30"), the release behaviors of the HSA were compared at various pH values. This example was performed to see the ability of the micelles to release the HSA depending on the formation of the ionic complexes.

Example 14

After 5 mol of HSA was contained in the PEG-PAE-API block copolymer prepared in Example 1 to form HSA-containing block copolymeric micelles ("API50"), the release behaviors of the HSA were compared at various pH values. This example was performed to see the ability of the micelles to release the HSA depending on the formation of the ionic complexes.

Comparative Example 1

A PEG-PAE-API block copolymer having a number average molecular weight ($M_n$) of 9,800 was prepared in a yield of 95% in the same manner as in Example 1, except that A-PEG prepared using MPEG 400 instead of MPEG 5000 was used in an amount of 10 mol.

The behavior of the PEG-PAE-API block copolymer was observed with varying pH values, and as a result, it was confirmed that the block copolymer did not form micelles. As described above, the hydrophilic blocks of the block copolymer were too short in length to induce self-assembly of the block copolymer resulting from the hydrophilic/hydrophobic balance at a particular pH, making it difficult to form micelles. This result proves that although formed, the micelles were dissolved in water and were liable to collapse.

Comparative Example 2

A PEG-PAE-API block copolymer having a number average molecular weight ($M_n$) of 21,000 was prepared in the same manner as in Example 1, except that A-PEG prepared using MPEG 12000 instead of MPEG 5000 was used in an amount of 10 mol.

The behavior of the PEG-PAE-API block copolymer was observed with varying pH values, and as a result, it was confirmed that the block copolymer did not form micelles, like the block copolymer prepared in Comparative Example 1. This result implies that the length of the block was too long compared to the molecular weight of the hydrophobic poly (amino acid), causing hydrophilic/hydrophobic imbalance, and the block copolymer did not form micelles at a particular pH and precipitated.

Experimental Example 1

Measurement of Molecular Weights of the pH Sensitivity Block Copolymers

GPC analysis was performed to measure the molecular weights of the pH-sensitive block copolymers (PEG-PAE-API, PEG-PAEA-API and PEG-PAA-API) prepared in Examples 1-10.

Experimental Example 2 pK Measurement of the Block Copolymers by Acid-Base Titration

Figure 4:
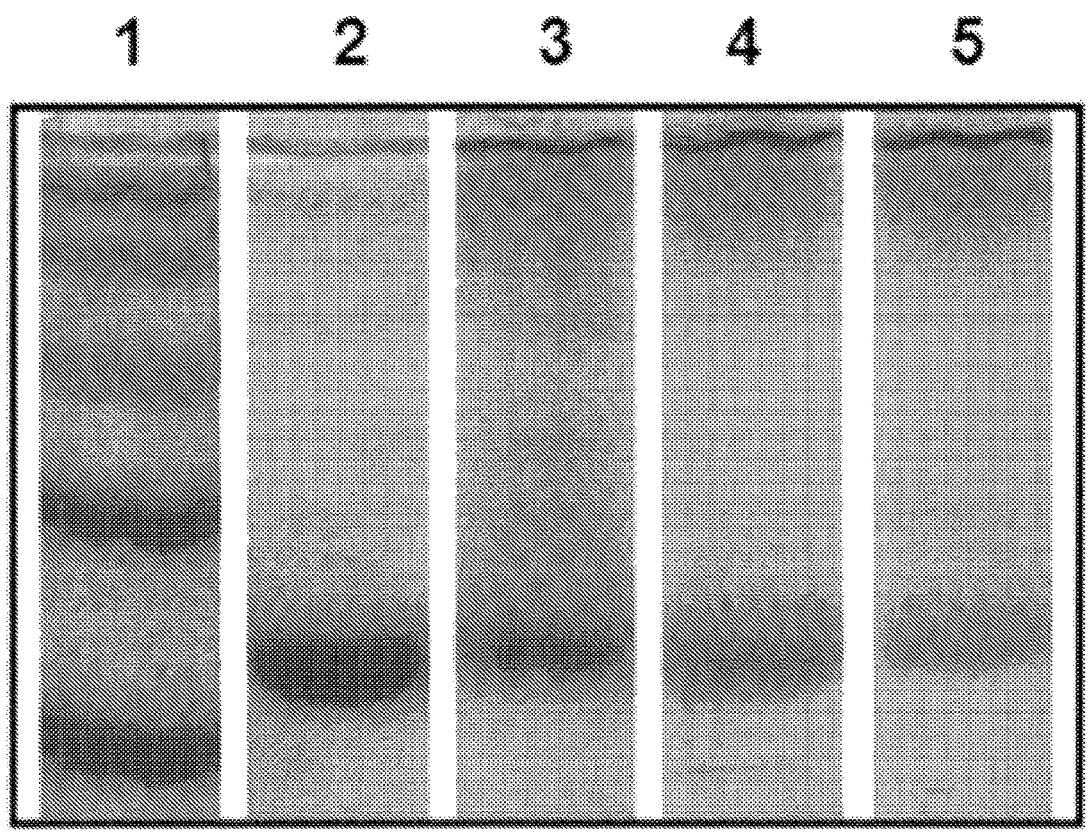
FIG. 4 shows electrophoresis images of human serum albumin (HSA) and pH-sensitive block copolymers prepared in Examples 1-3 and 11 at pH 7.4: Lane 1: molecular weight marker, Lane 2: pure HSA, Lane 3: API10+HSA, Lane 4: API30+HSA, Lane 5: API50+HSA (5 wt % HSA of polymer and 200 ng/mL HSA for each sample in water)
Figure 5:
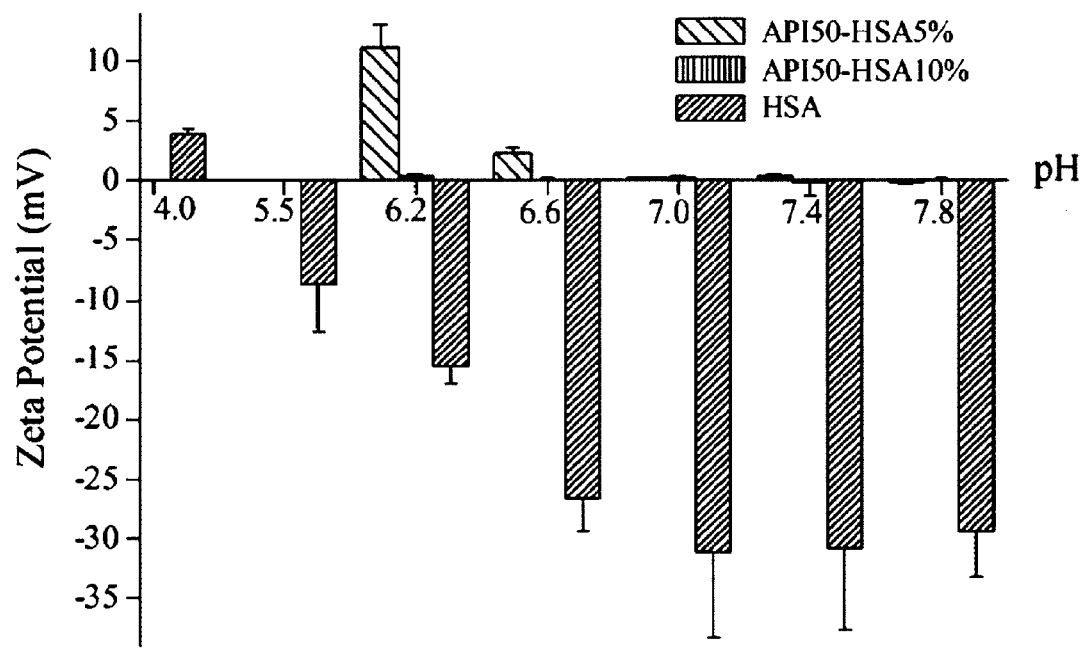
FIG. 5 is a graph showing zeta potentials of micelles composed of a block copolymer prepared in Example 1 and a protein contained in the block copolymer, micelles composed of a block copolymer prepared in Example 2 and a protein contained in the block copolymer, and pure HSA at various pH values.

The pK values of the pH-sensitive block copolymers having different API contents prepared in Examples 1-3 were measured, and the results are shown in FIG. 4.

FIG. 4 shows that the inflection points of the acid-base titration drastically varied and the pK values slightly increased with increasing API content.

Experimental Example 3

Measurement of Zeta Potentials of Micelles and HSA with Varying pH Values

Figure 6:
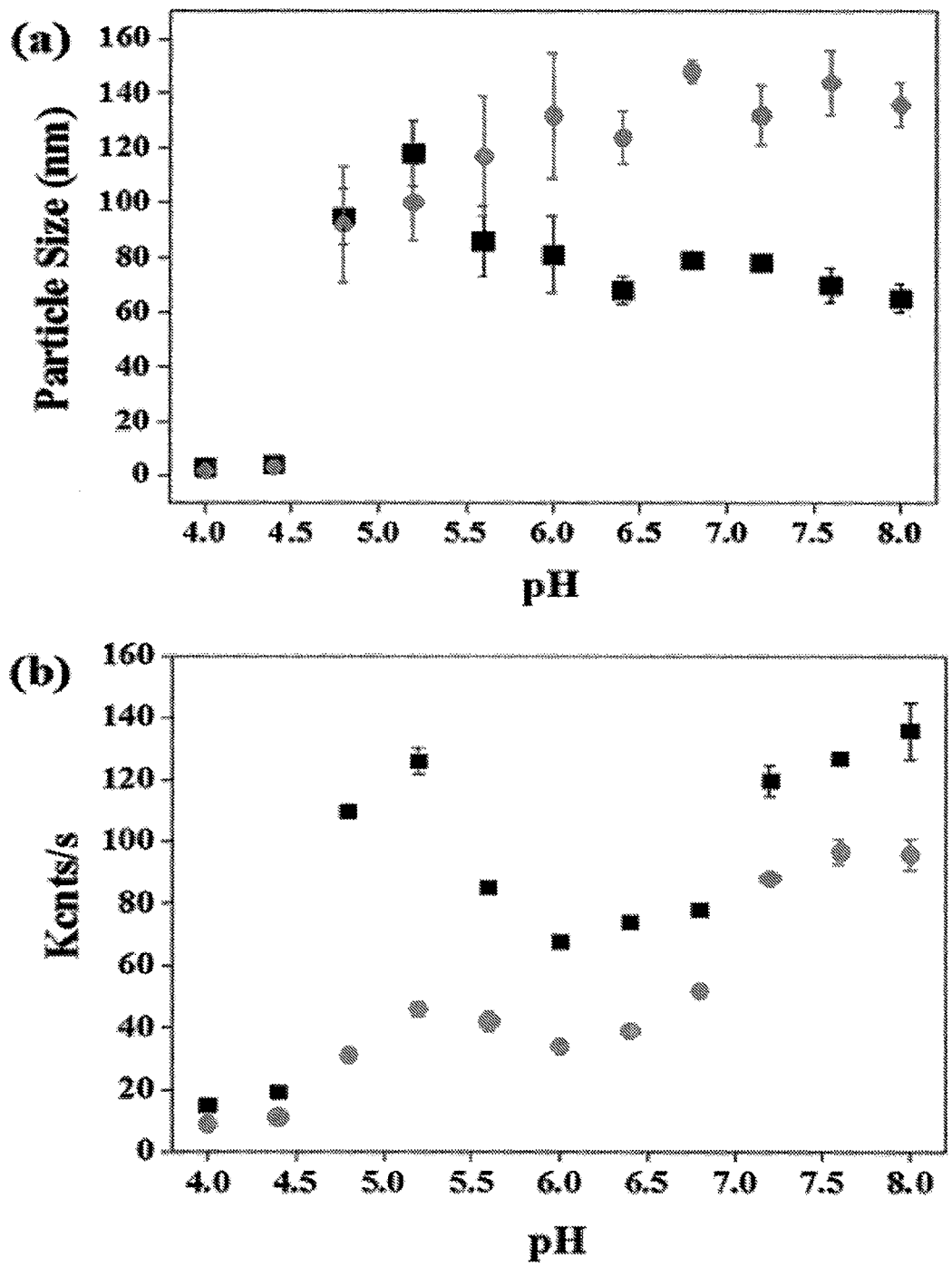
FIG. 6 graphically shows changes in the particle size (a) and scattering intensity (b) of micelles depending on the presence or absence of salts of block copolymers prepared in Examples 1-3 with varying pH values, as measured dynamic light scattering (DLS)

The zeta potential of the pH-sensitive block copolymer prepared in Example 1 and the zeta potential of micelles composed of the block copolymer and pure HSA contained in the block copolymer were measured at various pH values and the results are shown in FIG. 6.

FIG. 6 shows that the pure HSA was negatively charged at pH≥5.5 and was positively charged at pH<5.5. The HSA-containing sample was positively charged at pH<6.6 and was neutralized at pH≥6.6.

Experimental Example 4

Evaluation of Stability of Micelle-HSA Particles with Varying pH Values

After HSA was contained in each of the block copolymers prepared in Examples 1 and 11, variations in the particle size of the HSA-containing micelles were observed with the passage of time to evaluate the stability of the micelles and the HSA particles. The results are shown in FIG. 7.

Figure 7:
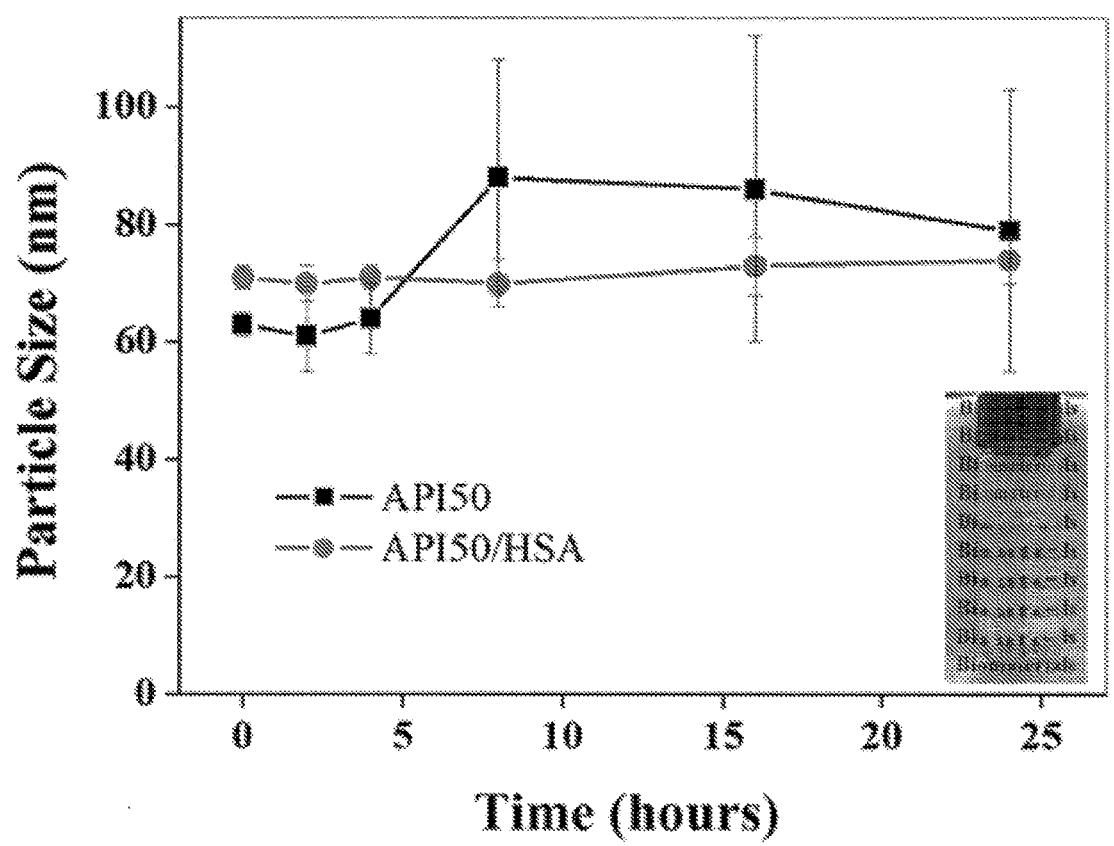
FIG. 7 is a graph showing changes in the particle size of micelles composed of a block copolymer prepared in Example 3 and pure HSA contained in the block copolymer, and micelles composed of a block copolymer prepared in Example 11 and pure HSA contained in the block copolymer with time, as measured by DLS.

As shown in FIG. 7, the particle size of the HSA-containing micelles remained significantly unchanged for 24 hr, demonstrating the formation of strong ionic complexes of the micelles and the HSA.

Experimental Example 5

Evaluation of Release Behavior of Micelle-HSA with Varying pH Values

After HSA was contained in each of the block copolymers prepared in Examples 3 and 11, the amount of the HSA released from the micelles was measured with varying pH values. The results are shown in FIG. 8.

Figure 8:
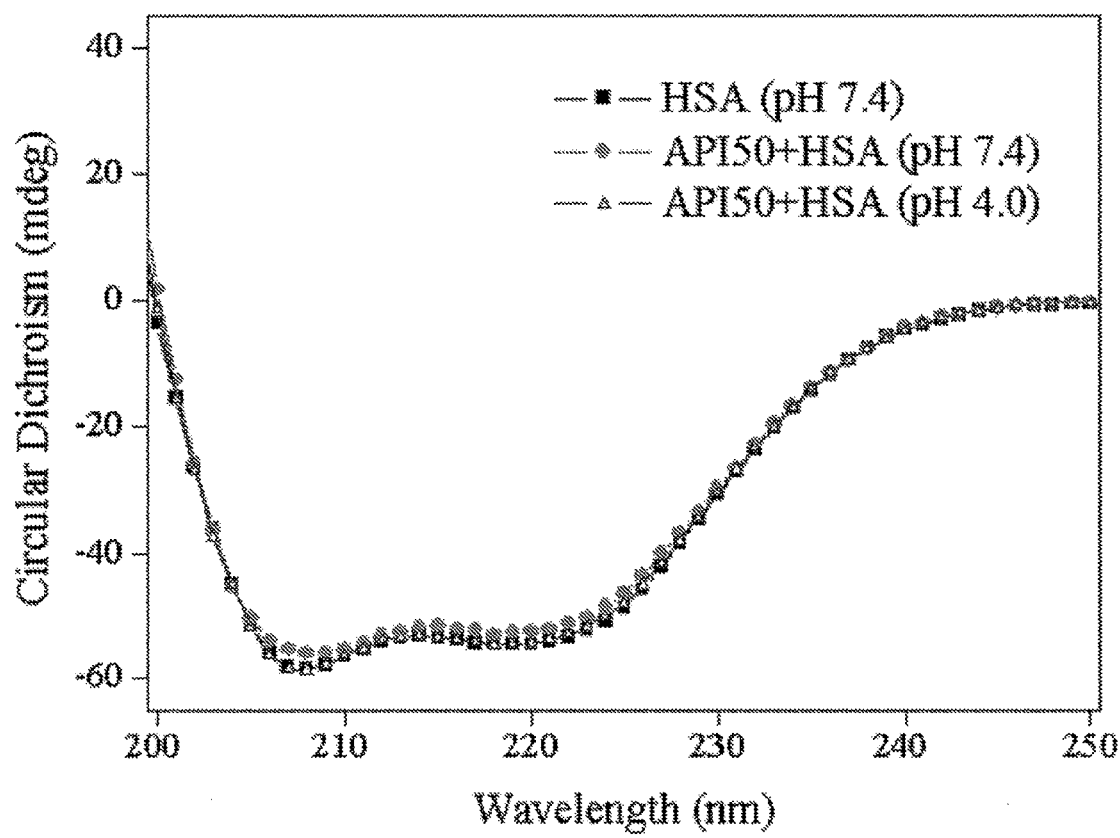
FIG. 8 is a graph showing changes in the amount of pure HSA released from micelles composed of a block copolymer prepared in Example 3 and the pure HSA contained in the block copolymer, and micelles composed of a block copolymer prepared in Example 11 and the pure HSA contained in the block copolymer, as measured by circular dichroism (CD): (■) HSA, (●) complexed HSA and (Δ) released HSA.
Figure 9:
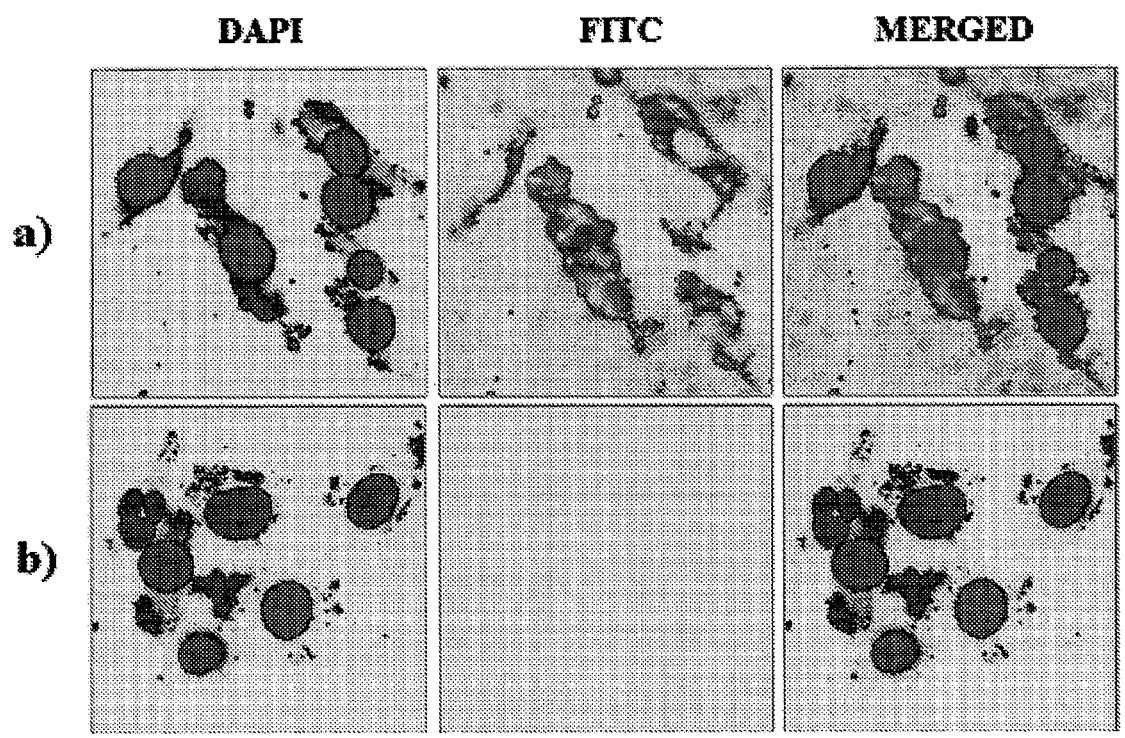
FIG. 9 shows confocal microscopy images of FITC-labeled HSA and PIC micelles composed of a block copolymer prepared in Example 3 and FITC-labeled pure HSA after incubation in MDA-MB-435 cells to observe the intracellular penetration of the labeled HSA: (a) FITC-labeled PIC micelles and (b) HSA-FITC (green color) distribution in cytoplasm.
Figure 10:
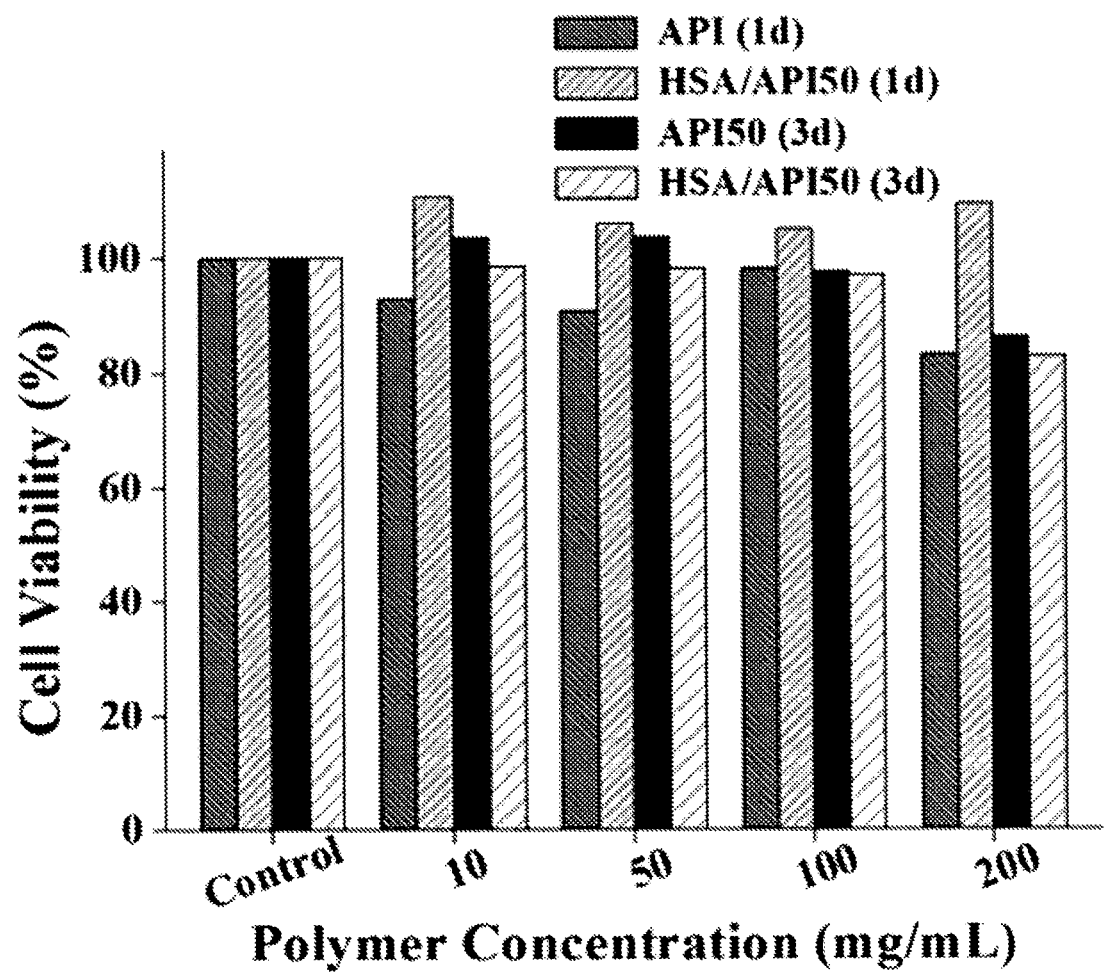
FIG. 10 is a graph showing in vitro cytotoxicity of micelles composed of a block copolymer prepared in Example 3 and pure HSA contained in the block copolymers, and in vitro cytotoxicity of micelles composed of a block copolymer prepared in Example 11 and pure HSA contained in the block copolymers after incubation in MDA-MB-435 cells, as determined by MTT assay.

FIG. 8 shows that the release behavior of the HSA-containing micelles was in agreement with that of the HSA, revealing that the HSA stably contained in the micelles was completely released.

These experimental results lead to the conclusion that polymeric micelles of the pH-sensitive block copolymer according to the present invention may be formed and collapse due to the amphiphilicity and reversible self-assembly of the block copolymer with varying pH values. It can also be concluded that HSA forms strong ionic complexes with the micelles, is stably contained in the micelles and is completely released in response to pH variations.

As is apparent from the foregoing, the block copolymer of the present invention forms polyionic complex micelles and is prepared using the poly(amino acid), for example, a poly (β-amino ester) or poly(β-amido amine) compound, which is soluble in water depending on pH variations but does not form micelles through self-assembly, the hydrophilic polyethylene glycol compound and the heterocyclic alkyl amine compound. The heterocyclic alkyl amine compound is added during copolymerization of the poly(amino acid) with the polyethylene glycol compound to impart the ability to form strong ionic complexes of the micelles and a drug or protein.

The block copolymer of the present invention possesses pH sensitivity and forms polymeric micelles by reversible self-assembly. In addition, the block copolymer of the present invention can stably contain a drug or protein in the body and can release the drug or protein in response to pH variations at a disease site. Specifically, the block copolymer of the present invention is self-assembled at a pH higher than the isoelectric point (pI) of protein but lower than 7.4 to form polyionic complex micelles with a drug or protein in a nanometer-sized core-shell structure capable of stably containing the drug or protein and releasing the drug or protein at a pH of less than the isoelectric point (pI) by charge repulsion between the block copolymer and the drug or protein. Therefore, the block copolymer of the present invention can be used as a target-specific drug or protein carrier and in diagnostic applications.

Although the present invention has been described herein with reference to the foregoing embodiments and accompanying drawings, the scope of the present invention is not limited to the embodiments. Therefore, it will be evident to those skilled in the art that various substitutions, modifications and changes are possible, without departing from the spirit of the invention as disclosed in the accompanying claims.

What is claimed is:

1. A pH-sensitive block copolymer forming polyionic complex micelles, which is prepared by copolymerization of: (a) a polyethylene glycol compound; (b) a poly(amino acid) compound; and (c) a heterocyclic alkyl amine compound having the ability to induce the formation of ionic complexes, wherein the heterocyclic alkyl amine compound is selected from the group consisting of 1-(3-aminopropyl)imidazole, 1-(2-aminoethyl)pyrrolidine, 2-(2-aminoethyl)-1-methylpyrrolidine, N-(3-aminopropyl)-2-pipecoline, N-(N-methyl-N-benzene)-1-propylamine, N-(3-aminopropyl)-2-pyrrolidinone, 2-(2-pyridyl)ethylamine, 4-(2-aminoethyl) morpholine, 3-morpholinopropylamine, histidine, and mixtures thereof.

2. The pH-sensitive block copolymer according to claim 1, wherein the polyethylene glycol compound has an acrylate or methacrylate group as a monofunctional group at one end thereof.

3. The pH-sensitive block copolymer according to claim 1, wherein the polyethylene glycol compound has a number average molecular weight ($M_n$) of 500 to 5,000 g/mol.

4. The pH-sensitive block copolymer according to claim 1, wherein the poly(amino acid) compound is a poly(β-amino ester) (PAE), a poly(β-amido amine) (PAA) or a copolymer thereof (PAEA).

5. The pH-sensitive block copolymer according to claim 1, wherein the poly(amino acid) compound is prepared by polymerization of a bisacrylate or bisacrylamide compound with a primary or secondary amine compound.

6. The pH-sensitive block copolymer according to claim 5, wherein the bisacrylate compound is selected from the group consisting of ethylene glycol diacrylate, 1,4-butanediol diacrylate, 1,3-butanediol diacrylate, 1,6-hexanediol diacrylate, 1,5-pentanediol diacrylate, 2,5-pentanediol diacrylate, 1,6-hexanediol ethoxylate diacrylate, 1,6-hexanediol propoxylate diacrylate, 3-hydroxy-2,2-dimethylpropyl-3-hydroxy-2,2-dimethylpropionate diacrylate, 1,7-heptanediol diacrylate, 1,8-octanediol diacrylate, 1,9-nonanediol diacrylate, 1,10-decanediol diacrylate, and mixtures thereof; and the bisacrylamide compound is N,N'-methylene bisacrylamide (MDA) or N,N'-ethylene bisacrylamide.

7. The pH-sensitive block copolymer according to claim 5, wherein the primary amine compound is selected from the group consisting of 1-methylamine, 1-ethylamine, 1-propylamine, 1-butylamine, 1-pentylamine, 1-hexanamine, 1-heptanamine, 1-octanamine, 1-nonanamine, 1-decanamine, 1-isopropylamine, triethyleneamine, 3-methoxypropylamine, 3-ethoxypropylamine, 3-isopropoxy-1-propanamine, 3-propyl-1-propanamine, 3-butoxy-1-propanamine, 1,4-dioxa-1-ethoxyamine, 4,4-dimethoxybutylamine, 4,4-diethoxy-1-butanamine, 2-methoxyethanamine, 3-ethoxyethanamine, 3-isopropoxy-1-ethoxyethanamine, 4,4-dimethoxyethylamine, 4,4-diethoxy-1-ethylamine, tetrahydro-2-furanylmethylamine, 2-phenoxyethanamine, 2-(3,4-dimethoxyphenyl)ethanamine, 2-(2,5-dimethoxyphenyl)ethylamine, 1,2,2,-trimethyl-1-propanamine, 2-methyl-1-butanamine, 3-methyl-1-butanamine, 1,3-dimethyl-1-butanamine, 4-methyl-1-pentanamine, 3,3-dimethyl-1-butanamine, 1,4-dimethyl-1-pentanamine, 1-methyl-1-hexanamine, 1-methyl-1-heptanamine, 2-ethyl-1-hexanamine, 2-aminoethanol, 3-amino-1-propanol, (2R)-1-amino-2-propanol, (2S)-1-amino-2-propanol, 2-amino-1-propanol, (2S)-1-amino-2-propanol, 2-amino-1,3-propanediol, 2-amino-2-methyl-1,3-propanediol, 2-amino-2-methyl-1-propanol, 4-amino-1-butanol, 2-amino-1-propanol, 2-ethylamino-1-butanol, 2-(2-aminoethoxy)ethanol, 5-amino-1-pentanol, 3-amino-2,2-dimethyl-1-propanol, 2-amino-2-ethyl-1,3-propanediol, 2-amino-3-methyl-1-butanol, 6-amino-1-hexanol, (1-aminocyclopentyl)methanol, 4-aminocyclohexanol, 2-aminocyclohexanol, 2-methyl-1-propanamine, cyclobutanamine, cyclopropylmethylamine, cyclopentanamine, cyclohexanamine, cyclohexanmethylamine, adamantanemethylamine, Si-methyl-diethoxy-propylamine, Si-trithoxypropylamine, 1,4-diazepane, N,N'-diethyl-1,2-ethanediamine, N,N'-diisopropyl-1,2-ethanediamine, N,N'-dimethyl-1,2-propanediamine, N,N'-dimethyl-1,3-propanediamine, N,N'-diethyl-1,3-propanediamine, N,N'-diethyl-1,4-pentanediamine, N,N'-bis(2-hydroxyethyl)ethylenediamine, N,N'-bis(2-hydroxyethyl)propylenediamine, and mixtures thereof; and the secondary amine compound is selected from the group consisting of 4,4'-trimethylenepiperidine, N,N'-dimethylethylenediamine, piperazine, 2-methylpiperazine, 3-methyl-4-(3-methylphenyl)piperazine, 3-methylpiperazine, 4-(phenylmethyl)piperazine, 4-(1-phenylethyl)piperazine, 4-(1,1'-dimethoxycarbonyl)piperazine, 4-(2-(bis(2-propenyl)amino)ethyl)piperazine, 1-(2-aminoethyl)piperazine, 4-(aminomethyl)piperazine, N,N'-dimethyl-1,2-ethanediamine, N,N'-diethyl-1,2-ethanediamine, N,N'-diisopropyl-1,2-ethanediamine, N,N'-dimethyl-1,2-propyldiamine, N,N'-diethyl-1,2-propyldiamine, N,N'-diisopropyl-1,2-propyldiamine, N,N'-dimethyl-1,2-hexanediamine, N,N'-dimethyl-N-[3-(methylamino)propyl]-1,3-propanediamine, N-[2-(methylamino)ethoxyethyl]-N,N'-dimethylamine, N-[2-(methylamino)dioxyethyl]-N,N'-dimethylamine, 1,4-diazepane, and mixtures thereof.

8. The pH-sensitive block copolymer according to claim 1, wherein the pH-sensitive block copolymer has a molecular weight of 1,000 to 20,000 g/mol.

9. A drug or protein carrier comprising the pH-sensitive block copolymer according to any one of claims 1 to 7 and 8, the copolymer comprising: a hydrophilic block derived from the polyethylene glycol compound; a hydrophobic block derived from the poly(amino acid) compound; and tertiary amine groups ionizable at pH 6.0~7.0 between the two blocks, wherein the pH-sensitive block copolymer forms micelles in the pH range of 7.0-7.4 by reversible self-assembly, the heterocyclic alkyl amine compound induces the formation of polyionic complexes with the micelles, and the polyionic complexes stably contain a drug or protein during circulation along blood vessels of a human body and release the drug or protein at a disease site.

10. The drug or protein carrier of claim 9, wherein the drug or protein is an anticancer agent selected from the group consisting of human serum albumin (HSA), paclitaxel, doxorubicin, retinoic acids, cis-platin, camptothecin, fluorouracil (5-FU), docetaxel, tamoxifen, anasterozole, carboplatin, topotecan, belotecan, irinotecan, gleevec and vincristine, an anti-inflammatory agent selected from the group consisting of aspirin, salicylates, ibuprofen, naproxen, fenoprofen, indomethacin, phenyltazone, methotrexate, cyclophosphamide, mechlorethamine, dexamethasone, prednisolone, celecoxib, valdecoxib, nimesulide, cortisone and corticosteroid, or a mixture thereof; and is released when the micelle particles collapse locally at pH<7.0 at a cancer or inflammatory disease site.

11. The drug or protein carrier of claim 10, wherein a cancer disease at the cancer disease site is breast cancer, lung cancer, uterine cancer, cervical cancer, prostate cancer, pharyngeal cancer, pancreatic cancer, brain tumor, liver cancer, skin cancer, esophageal cancer, testicular cancer, renal cancer, colorectal cancer, thyroid cancer, tongue cancer or rectal cancer.

12. The drug or protein carrier of claim 10, wherein an inflammatory disease at the inflammatory disease site is rheumatoid arthritis, osteoarthritis or arteriosclerosis.

* * * * *